United States Patent [19]

Kronenthal

[11] Patent Number: 5,081,266
[45] Date of Patent: Jan. 14, 1992

[54] PROCESS FOR PREPARING [1S-[1α,2α(Z),3α,4α]]-7-[3-[[[[(1-OXOHEPTYL)-AMINO]ACETYL]AMINO]METHYL]-7-OXABICYCLO-[2.2.1]HEPT-2-YL]-5-HEPTENOIC ACID

[75] Inventor: David Kronenthal, Yardley, Pa.

[73] Assignee: E. R. Squibb & Sons, Inc., Princeton, N.J.

[21] Appl. No.: 588,383

[22] Filed: Sep. 26, 1990

Related U.S. Application Data

[62] Division of Ser. No. 484,307, Feb. 26, 1990, Pat. No. 4,978,762.

[51] Int. Cl.$^5$ .......................................... C07D 307/00
[52] U.S. Cl. ............................................. 549/463
[58] Field of Search ................................. 549/463

[56] References Cited

U.S. PATENT DOCUMENTS 4,663,336 5/1987 Nakane ..................... 549/463 X
4,687,865 8/1987 Thottathil ................... 549/463

FOREIGN PATENT DOCUMENTS 2005264 4/1979 United Kingdom .

OTHER PUBLICATIONS

D. Mitsunobu, "The Use of Diethyl Azodicarboxylate and Triphenyl-phosphine", Synthesis, 1981 pp. 1–28.
A. Meyers et al., "Highly Stereoselective Route", J. Org. Chem. 1981, 46, pp. 3119–3123.
Bender, "General Acid–Base Catalysis", J. Am. Chem. Soc. 1957, 79, pp. 1258–1259.
Mitsunobu et al., Journal of the American Chemical Society, vol. 94, No. 2 (1972) pp. 679–680.
G. Verlay; Houben–Weyl: "Methoden der Organischen Chemie", vol. XI/1, 1957, pp. 94–96.

Primary Examiner—Catherine S. Kilby Scalzo
Attorney, Agent, or Firm—Suzanne E. Babajko

[57] ABSTRACT

A new process for preparing [1S-[1α,2α(Z),-3α,4α]]-7-[3-[[[[(1-oxoheptyl)-amino]acetyl]amino]methyl]-7-oxabicyclo [2.2.1]-hept-2-yl]-5-heptenoic acid. New intermediates are also described. [1S-(1α,2α(9Z),3α,-4α]]-7-[3-[[[[(1-oxoheptyl)-amino]acetyl]amino]methyl]-7-oxabicyclo[2.2.1]hept-2-yl]-5-heptenoic acid is useful in the treatment of thrombotic disease.

2 Claims, No Drawings

1

PROCESS FOR PREPARING [1S-[1α,2α(Z),3α,4α]]-7-[3-[[[[(1-OXOHEPTYL)-AMINO]ACETYL]AMINO]METHYL]-7-OXABICY-CLO-[2.2.1]HEPT-2-YL]-5-HEPTENOIC ACID

This is a continuation division of application Ser. No. 484,307, filed on Feb. 26, 1990 now U.S. Pat. No. 4,978,700.

BACKGROUND OF THE INVENTION

[1S-[1a, 2a(Z), 3a, 4a]]-7-[3-[[[[(1-oxoheptyl)amino]acetyl ]amino]methyl]-7-oxabicyclo[2.2.1]hept-2-yl]-5-heptenoic acid is a useful cardiovascular agent which can be used, for example, in the treatment of thrombotic disease. A synthesis of this compound is described in U.S. Pat. No. 4,663,336 issued on May 5, 1987. The patent describes a synthesis which is represented by the following scheme.

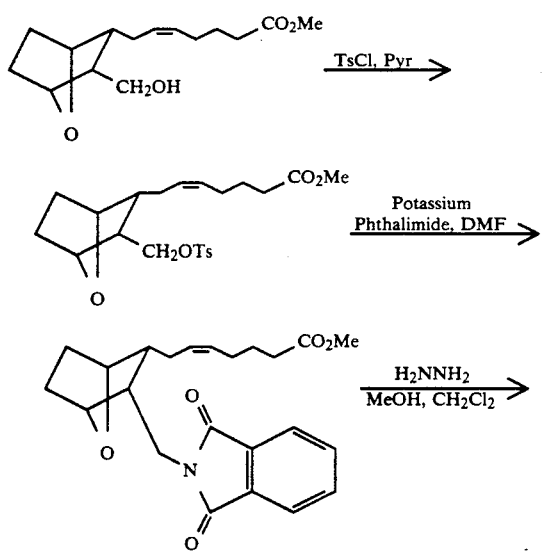

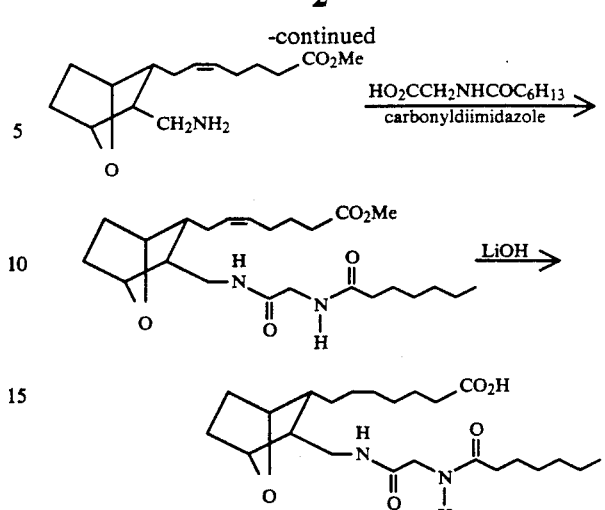

However, the above process involves the use of hydrazine (NH$_2$NH$_2$) which results in the formation of undesirable side products such as compounds having the formula

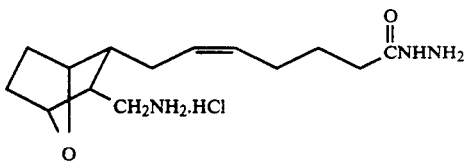

SUMMARY OF THE INVENTION

It has now been discovered that in situ formation of intermediate 2 followed by a two step hydrolysis reaction of the phthalimide moiety carried out with a) strong base and b) an aqueous acid can overcome the shortcomings of the previous method. The process of the present invention results in higher overall yields of the final product, and eliminates the use of hydrazine and the problems associated with its use (i.e. the formation of hydrazide by-products)

The process of this invention can be represented by the following scheme:

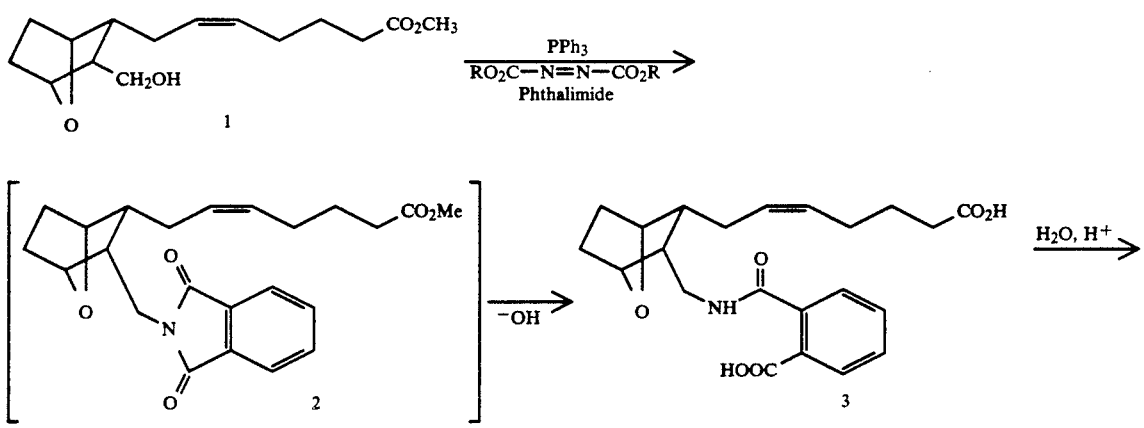

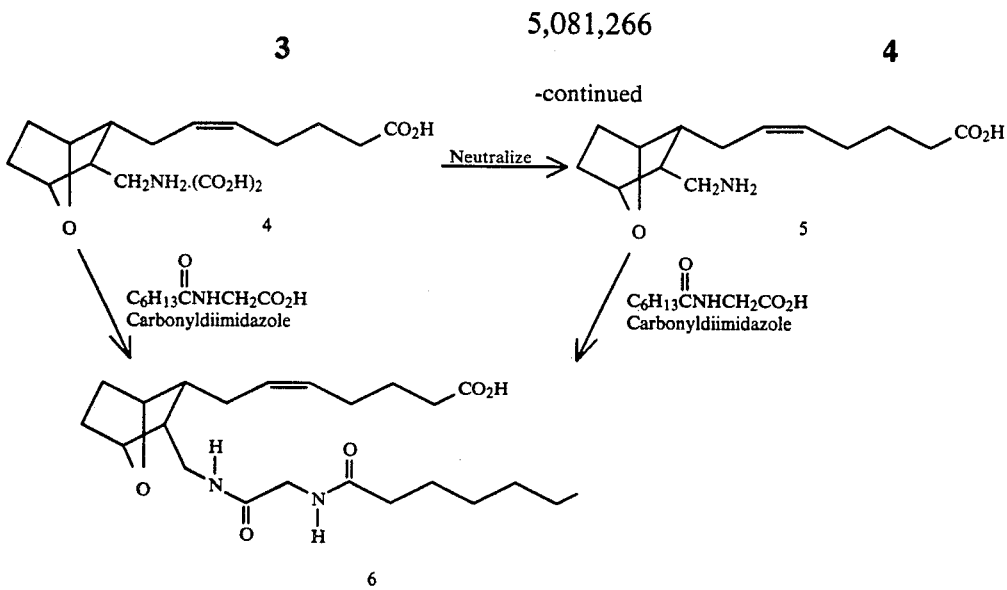

DETAILED DESCRIPTION OF THE INVENTION

Compound 1 is converted directly to the phthalimide 2- by treatment with triphenylphosphine, an azodicarboxylate ester such as diethylazodiacarboxylate (DEAD) or diisopropylazodicarboxylate (DIAD) and phthalimide. For example, the DIAD is added dropwise to a mixture of the above components in an organic solvent such as dichloromethane, toluene or tetrahydrofuran while maintaining a temperature of about 20° C. to about 25° C. The reaction mixture is then stirred at room temperature for an additional four to twelve hours. Compound 2- is then hydrolyzed to the phthalamic diacid 3-. This is accomplished by treatment of compound 2 with strong base such as sodium hydroxide, potassium hydroxide, or lithium hydroxide. The reaction may be run in the presence of an organic cosolvent such as tetrahydrofuran. Compound 3 is then hydrolyzed with water and aqueous acid in the presence of an organic cosolvent such as tetrahydrofuran. The reaction is conducted at a temperature of 25° C.-70° C. and optimally at 60° -65° C. Either mineral acids (such as HCl) or an organic acid such as oxalic, or citric acid, may be employed in the hydrolysis. The resulting amino acid is obtained as the conjugate acid (the exact nature of which depends on the acid used in the hydrolysis). When oxalic acid is employed and THF is the organic co-solvent the amino acid oxalate salt 4 precipitates directly from the reaction mixture on cooling. Compound 4 can be converted directly to compound 6- by acylation with [(1-oxoheptyl)amino]acetic acid at 0° C. under argon in the presence of a coupling agent such as 1,1-carbonyldiimidazole and a tertiary amine base such as N,N-diisopropylethylamine, tributylamine or 1,8-Diazabicyclo[5.4.0]undec7-ene.

Alternatively, if the level of trans double bond contamination (from the previous Wittig reaction used to prepare 2) in compound 4 is unacceptably high, the oxalate salt 4 is neutralized to the free amino acid 5. This is accomplished by treatment with a base such as triethylamine accompanied with stirring for ten to twelve hours. Alternatively, neutralization may be accomplished by using an ion-exchange resin or inorganic base such as sodium or potassium hydroxide, carbonate or bicarbonate. Compound 5 is then acylated with [(1-oxoheptyl)amino]acetic acid. The reaction is carried out at about 0° C for about five hours.

Intermediates 3, 4 and 5 are novel and form an integral part of this invention.

The following examples are specific embodiments of this invention.

EXAMPLE 1

[1S-[1a, 2a(Z),3a, 4a]]-7-[3-[[[[(1-oxoheptyl)amino]acetyl]amino]methyl]-7-oxabicyclo[2.2.1]hept-2-yl]-5-heptenoic acid

EXAMPLE 1a

[1S-[1a, 2a(Z),3a, 4a]]-7-[(3-aminomethyl)-7-oxabicyclo[2.2.1]hept-2-yl]-5-heptenoic acid, oxalate (1:1)salt.

A dry 500 ml flask equipped with stirrer, argon (nitrogen) inlet, thermometer and dropping funnel was charged with [1S-[1a,2a(Z),3a,4a]]-7-[(3-hydroxymethyl)-7-oxabicyclo [2.2.]hept-2-yl]-5-heptenoic acid, methyl ester (20.007 gm, 74.65 mmole), triphenylphosphine (22.518 gm, 85.85 mmole) and dichloromethane (270 ml from a freshly or recently opened bottle). After stirring several minutes to obtain a clear solution, finely ground phthalimide (12.0S2 gm, 82.12 mmole) was added. While maintaining the internal temperature at 20°-25° C. with a water bath a solution of diisopropylazodicarboxylate (16.907 m, 93.61 mmole) in dichloromethane (45 ml) was added dropwise over 30 minutes. After the addition, the reaction was stirred at room temperature for 4hours.

The solvent was removed in vacuo to a heavy oil which was dissolved in toluene (50 ml). The resulting solution was washed with ice cold 0.25 M NaOH (3×80 ml), cold water (1×80 ml) and brine (1×80 ml). The toluene solution was dried over sodium sulfate, filtered and concentrated to a heavy oil, which was dissolved in tetrahydrofuran (350 ml) and treated (under argon) via a dropping funnel with a solution of lithium hydroxide monohydrate (10.964 gm, 261.29 mmole) in 260 ml of distilled water. The reaction was vigorously stirred under argon for 2 hours and acidified to pH 9.6 with about 20 ml of concentrated hydrochloric acid (added dropwise over ca. 15 minutes)

The reaction was transferred to an evaporating flask and 330 ml of solvent was removed in vacuo at ≦30° C. Ethyl acetate (250 ml) was immediately added to the residue and the mixture was transferred to a separatory funnel and shaken. The organic layer was discarded and the aqueous layer was washed with additional ethyl acetate (3×250 ml).

The product rich aqueous layer was stirred while adjusting the pH from 8.8 to 7 with several drops of concentrated hydrochloric acid. Ethyl acetate (400 ml) was added and the resulting two phase system was vigorously stirred while lowering the pH of the aqueous layer to two.

After transferring to a separatory funnel and separating the layers, the aqueous layer was washed with additional ethyl acetate (2×100 ml). The combined product rich organic layers were washed with half-saturated brine (1×240 ml) and brine (1×200 ml) and dried over sodium sulfate. The organic solution was filtered and concentrated in vacuo at ≦30° C. The resulting solid phthalamic acid derivative (3) was dried under high vacuum to 9.17 gm.

The phthalamic acid was dissolved in tetrahydrofuran (150 ml) and evaporated to remove traces of ethyl acetate. The material was redissolved in tetrahydrofuran (243 ml including the amount left after the evaporation) and added to a 500 ml flask equipped with mechanical stirrer and argon inlet. Anhydrous oxalic acid (13.437 gm, 149 mmole) was added followed by water (68 ml). The resulting hazy solution was stirred at a gentle reflux under argon for 6.5 hours. Heating was discontinued and the mixture stirred overnight.

The resulting crystal slurry was stirred while cooling at 0° C. for 4 hours. The product was filtered and washed with tetrahydrofuran (2×140 ml), ethyl acetate (3×140 ml) and hexane (3×140 ml). The title compound was dried under high vacuum, initially at room temperature to a constant weight of 18.899 gm, and then at 50° C. overnight to 18.880 gm. M.P. =184°-187° C.

EXAMPLE 1b

[1S-[1a,2a(Z),3a,4a]]-7-[3-[[[[(1-oxoheptyl)-amino]acetyl]amino]methyl]-7-oxabicyclo[2.2.1]hept-2-yl]-5-heptenoic acid A suspension of [(1-oxoheptyl)amino] acetic acid (2.673 g, 14.273 mmole) in dichloromethane (80 ml) was stirred under argon at 0° C. and treated with solid 1,1-carbonyldiimidazole (CDI; 2.25 g, 13.873 mmole) over 3 minutes. The resulting suspension was stirred briefly at 0° C. and then at room temperature for 2.5 hours. The resulting solution was cooled to 0° C and treated with solid [1S [1a,2a(Z),3a,4a]]-7-[3-aminomethyl)-7-oxabicyclo2.2.1]hept-2-yl]5acid, oxalate (1:1) salt (4.7 g, 13.339 mmole) followed by N,N-diisopropylethylamine (7.09 ml, 40.685 mmole). The reaction was stirred vigorously for 4 hours and treated with 1N HCl (40 ml). Additional HCl was then added to lower the pH of the aqueous layer to 2.5. The biphasic mixture was transferred to a separatory funnel, the layers were separated and the aqueous layer was extracted with dichloromethane (3×10 ml). The three organic extracts were added to the original dichloromethane layer and the resulting organic solution was washed with 1N HCl (3×50 ml), water (3×40 ml), and brine (1×50 ml).

The organic solution was concentrated in vacuo to a small volume, and ethyl acetate was added and evaporated. The resulting solid was recrystallized from ethyl acetate. The product was filtered, washed with ethyl acetate and hexane and dried in vacuo. The yield of the title compound was 4.895 g (86%). M.P.=117°-119° C.

EXAMPLE 2

[1S-[1a, 2a(Z),3a, 4a]]-7-[(3-aminomethyl)-7-oxabicyclo[2.2.1]hept-2-yl]-5-heptanoic acid.

A suspension of [1S-[1a,2a(Z),3a, 4a]-7-(3-aminomethyl)-7-oxabicyclo[2.2.1 hept-2-yl]-5-heptenoic acid, oxalate (1:1) salt (6.72 g corrected weight, 19.568 mmole; contained 2.25% trans olefin by HPLC) in methanol (70 ml) was stirred under argon and treated over 5 minutes with triethylamine (6.73 ml, 41.1 mmole). An additional 6 ml of methanol was added and the heavy slurry was stirred at room temperature overnight. The slurry was filtered and the crude product was washed with methanol, ether, and hexane and dried in vacuo to 3.55 g (72%) of the title compound containing 0.64% trans olefin by HPLC.

A portion of the product (3.0 g) was slurried in methanol-water (18 ml-4.5 ml) and stirred overnight. The slurry was filtered and washed with 15% aqueous methanol, methanol, ether and hexane. After drying in vacuo the product weighed 2.224 g and contained ≦0.05% trans olefin by HPLC. M.P.=233°-235° C. with decomposition.

EXAMPLE 2a

[1S-[1a, 2a(Z),3a, 4a]]-7-[(3-aminomethyl)-7-oxabicyclo[2.2.1]hept-2-yl]-5-heptenoic acid The mother liquors from a large scale run (606 g input of oxalate salt) were combined and concentrated in vacuo using toluene to remove water. The residue was slurried in methanol (3 L), stirred overnight and filtered to afford 294 g of [1S-[1a, 2a(Z),3a, 4a]]-7-[(3-aminomethyl) 7-oxabicyclo-[2.2.1]hept-2-yl]-5-heptenoic acid, hemioxalate salt. This material was slurried in methanol (2200 ml), treated with triethylamine (100.32 g) and stirred at room temperature overnight. The slurry was filtered and washed with methanol and ether to afford 217 g of the title compound.

EXAMPLE 3

[1S-[1a, 2a(Z),3a, 4a]]-7-3-[[[[(1-oxohectyl)amino]acetyl]amino]methyl]-7-oxabicyclo[2.2.1]hept-2-yl]-5-heptenoic acid A suspension of [(1-oxoheptyl)amino] acetic acid (102.75 g, 0.55 mol) in dichloromethane (2600 ml) was chilled to 0° C. under a gentle sweep of argon and treated with CDI (85.16 g), 0.525 mol) in one portion. The reaction mixture was stirred at 0° C. for five minutes then warmed to 25° C. over fifteen minutes. The reaction was then stirred at 25° C. (internal temperature maintained with a warm water bath) for three hours. The resultant solution was chilled to 0° C., treated with diisopropylethylamine (85.67 g, 0.66 mol), stirred for ~five minutes, then treated with powdered [1S-[1a, 2a(Z), 3a, 4a]]-7-[(3-aminomethyl)-7-oxabicyclo[2.2.-]hept2-yl]-5heptenoic acid, (129.7 g, 0.51 mol with residual water correction). The reaction slurry was stirred at 0°-2° C. for five hours.

The slurry was treated with 1800 ml of 1N HCl in one portion (exotherm to 22° C.), stirred for ~five minutes, then the layers were separated. The acidic aqueous layer (pH 2.1) was extracted with dichloromethane (3×400 ml). The combined organic layers were washed with 1N HCl (3×2 liter) and water (3×2 liter). Each aqueous was was extracted with dichloromethane (200 ml) and added to the main extract before each subsequent wash. The organic layer was dried over magnesium sulfate, filtered, and concentrated in vacuo to a dry solid (220 g).

The residue was combined with ethyl acetate (2550 ml) and heated until dissolution then left standing at room temperature overnight. The resultant solid was filtered and the solid washed sequentially on the frit with ethyl acetate (3×600 ml) and hexane (3×600 ml) to yield 170 g of the title compound. M.P. 116°-118° [a]$_D$=7.1° (c=1, MeOH).

EXAMPLE 4

[1S-[1a, 2a(Z),3a, 4a]-7-[(3-Aminomethyl)-7oxabicyclo-[2.2.1]hept-2-yl]-5-heptenoic acid A 3-necked flask equipped with overhead stirrer and reflux condenser was charged with [1S-[1a, 2a(Z),3a, 4a]]-7-[(3-aminomethyl)-7-oxabicyclo [2.2.1]hept-2-yl]-5-heptenoic acid, 1:1 oxalate Salt (10 g, 28.29 mmole after correction for residual water; 3.7trans double bond isomer by HPLC), methanol (60 ml), and water (8 ml). The mixture was cooled in an ice bath and treated with triethylamine (8.3 ml, 59.41 mmole). The cooling bath was removed and the slurry was stirred at ambient temperature for 20 minutes and then heated to reflux. Water was added slowly via the condenser until a clear solution was obtained (12-13° ml required- An additional 1 ml of water was then added, and the mixture was cooled while stirring and seeded at a bath temperature of 40° C. Stirring was continued at ambient temperature overnight, and then at 0° C. for several hours.

The product was filtered and washed with 5% aqueous methanol (3×10 ml), methanol (3×20 ml), ether (3×25 ml), and hexane (3×25 ml). The yield of the title compound was 4.8 g (68%). HPLC indicated the presence of 0.5% trans double bond isomer. M.P.=234°-235° C. with decomposition A slurry of 1 g of the product in 6 ml of methanol was treated with 2.5 ml of water. The resulting slurry was stirred at room temperature overnight and filtered. The product was washed with 70% methanol-water, methanol, ether, and hexane. The recovery of the title compound was 656 mg. HPLC analysis indicated <0.05% trans double bond isomer.

What is claimed is:

1. [1S-1a, 2a(Z), 3a, 4a]]-7-[(3-aminomethyl)-7-oxabicyclo[2.2.1]hept-2-yl]-5-heptenoic acid, oxalate (1:1) salt.

2. [1S-[1a, 2a(Z), 3a, 4,a]]-7-[3-[[(2-carboxybenzoyl)amino]methyl ]7-oxabicyclo[2.2.1]hept-2yl]-5-heptenoic acid.

* * * * *